United States Patent [19]

Cleugh et al.

[11] Patent Number: 5,334,744
[45] Date of Patent: Aug. 2, 1994

[54] ISOMERISATION PROCESS

[75] Inventors: Ernest S. Cleugh, Barnsley; David J. Milner, Manchester, both of England

[73] Assignee: Zeneca Ltd., London, England

[21] Appl. No.: 995,861

[22] Filed: Dec. 23, 1992

[30] Foreign Application Priority Data

Dec. 24, 1991 [GB] United Kingdom ............ 9127355.7

[51] Int. Cl.$^5$ ........................................... C07C 253/34
[52] U.S. Cl. ........................................ 558/354; 558/407
[58] Field of Search .............................. 558/354, 407

[56] References Cited

U.S. PATENT DOCUMENTS

| | | | |
|---|---|---|---|
| 3,401,178 | 9/1968 | Firestone et al. | 260/340.5 |
| 4,133,826 | 1/1979 | Warnant et al. | 260/465 D |
| 4,213,916 | 7/1980 | Davies et al. | 260/465 D |
| 4,308,279 | 12/1981 | Smeltz | 424/304 |
| 4,427,598 | 1/1984 | Masson et al. | 260/465 D |
| 4,512,931 | 4/1985 | Robson | 260/465 D |
| 4,544,508 | 10/1985 | Fuchs et al. | 260/465 D |
| 4,544,510 | 10/1985 | van Berkel et al. | 260/465 D |
| 4,670,464 | 6/1987 | Doyle et al. | 574/521 |
| 4,681,969 | 7/1987 | Williams et al. | 558/407 |
| 4,733,001 | 3/1988 | Suzuki et al. | 558/354 |
| 4,997,970 | 3/1991 | Ager | 558/354 |

FOREIGN PATENT DOCUMENTS

| | | |
|---|---|---|
| 0002289 | 6/1979 | European Pat. Off. |
| 040991 | 12/1981 | European Pat. Off. |
| 0050521 | 4/1982 | European Pat. Off. |
| 0107296 | 5/1984 | European Pat. Off. |
| 57-62298 | 4/1982 | Japan |
| 2001964 | 2/1979 | United Kingdom |
| 1582594 | 1/1981 | United Kingdom |
| 2130199 | 5/1984 | United Kingdom |

Primary Examiner—Joseph Paul Brust
Attorney, Agent, or Firm—Joel G. Ackerman

[57] ABSTRACT

A process for obtaining an isomer of a compound of general formula $$R-CH(CN)-R' \qquad (I)$$

wherein each of R and R' may be any organic radical linked directly or through a heteroatom to the carbon atom bearing the cyano group provided that at least one of R and R' comprises at least one resolved chiral center which is stable under the conditions of the process, or a racemic modification comprising the isomer and its enantiomer, which comprises the step of treating the epimer of the isomer, or the racemate comprising the epimer and the enantiomer of the epimer, in solution in a polar organic solvent, or in slurry in a polar organic liquid diluent in which the epimer or the racemate is partially soluble, with a source of cyanide ions, in the absence of a base, the isomer, or the racemic modification comprising the isomer and its enantiomer, being less soluble in the solvent or diluent than the epimer of the isomer, or the racemate comprising the epimer of the isomer and the enantiomer of the epimer, respectively.

9 Claims, No Drawings

ISOMERISATION PROCESS

This invention relates to a process for converting a first isomer into a second isomer wherein the first and second isomers are epimers of the same compound.

The present invention provides a process for obtaining an isomer of a compound of general formula

   (I)

wherein each of R and R' may be any organic radical linked directly or through a heteroatom to the carbon atom bearing the cyano group provided that at least one of R and R' comprises at least one resolved chiral centre which is stable under the conditions of the process, or a racemic modification comprising the isomer and its enantiomer, which comprises the step of treating the epimer of the isomer, or the racemate comprising the epimer and the enantiomer of the epimer, in solution in a polar organic solvent, or in slurry in a polar organic liquid diluent in which the epimer or the racemate is partially soluble, with a source of cyanide ions, in the absence of a base, the isomer, or the racemic modification comprising the isomer and its enantiomer, being less soluble in the solvent or diluent than the epimer of the isomer, or the racemate comprising the epimer of the isomer and the enantiomer of the epimer, respectively.

In a preferred aspect the process of the invention provides a means to obtain the isomer from its epimer where the epimer has been obtained by a production process in admixture with the isomer, and similarly it provides a means to obtain the racemic modification comprising the isomer and its enantiomer from the racemate comprising the epimer and the enantiomer of the epimer where the racemate has been obtained by a production process in admixture with the isomer and its enantiomer.

Although the process is generally applicable to the production of any isomer or racemic modification of a compound of formula I having the defined solubility characteristics, it is particularly useful for obtaining isomers and racemates of compounds wherein R is an ester group linked through the ether oxygen to the carbon atom bearing the cyano group and R' is an optionally substituted aryl or heteroaryl group. Within the group of such ester compounds may be found many which are useful as insecticides, such as for example, those wherein R is selected from 3-(2,2-dihalovinyl)-2,2-dimethylcyclopropylcarbonyloxy, 3-(2-optionally substituted phenyl-2-halovinyl)-2,2-dimethylcyclopropylcarbonyloxy, 3-(2-haloalkyl-2-halovinyl)-2,2-dimethylcyclopropylcarbonyloxy, 3-(2,2-dialkylvinyl)-2,2-dimethylcyclopropylcarbonyloxy, 3-(2-optionally substituted alkoxycarbonylvinyl)-2,2-dimethylcyclopropylcarbonyloxy, 3-(2-optionally substituted alkoxycarbonyl-2-halovinyl)-2,2-dimethylcyclopropylcarbonyloxy, and 2-(optionally substituted phenyl)alkanoyloxy, and R' is selected from phenyl optionally substuted by halo optionally substituted phenyl and optionally substituted phenoxy, and pyridyl optionally substituted by optionally substituted phenoxy. Such compounds are known generally as pyrethroids.

Pyrethroids are usually obtained by esterification processes which yield mixtures of isomers. It is known that some isomers have a greater insecticidal effect than others, and this has led to the development of techniques to separate the more active isomers, and to convert the less active isomers into the more active. Such processes have been described in for example UK patent no. 1582594, European patent no. 107296 and U.S. Pat. No. 4,997,970, and are all characterised by the use of a base. However under the conditions of these processes the base not only promotes the desired isomerisation by way of proton removal leading to epimerisation at the carbon atom bearing the cyano group but also, unfortunately, can catalyse the decomposition of the esters, leading to lowered yields of the desired product.

A number of such pyrethroid products comprising only one or two isomers have been commercialised such as deltamethrin (s-α-cyano-3-phenoxybenzyl 1R,3R-3-(2,2-dibromovinyl)-2,2-dimethylcyclopropane carboxylate), acrinathrin (S-α-cyano-3-phenoxybenzyl Z-1R,3S-3[2-(2,2,2-trifluoro-1-trifluoromethylethoxycarbonyl)vinyl]-2,2-dimethylcyclopropane carboxylate), S-fenvalerate (S-α-cyano-3-phenoxybenzyl S-2-(4-chlorophenyl)-3-methylbutyrate), and lambda-cyhalothrin (racemic combination of S-α-cyano-3-phenoxybenzyl 1R,3R-3-(Z-2-chloro-3,3,3-trifluoroprop-1-en-1-yl)-2,2-dimethylcyclopropane carboxylate and its enantiomer).

The invention process can be used to obtain deltamethrin, acrinathrin, S-fenvalerate and lambda-cyhalothrin from precursors products in which the desired isomer or racemate is admixed with its epimer or epimer racemate without the danger of loss of yield through base catalysed decomposition. In addition the process appears to operate on a reduced cycle time indicating that the use of cyanide mediated isomerisation offers an unexpected but significant economic advantage in comparison with the known base-catalysed epimerisation processes.

The exact mechanism by which the process of the invention leads to isomerisation of the epimer of the desired isomer to the product is not fully understood, but one possible explanation would involve the attack on the carbon atom bearing the cyano group by a cyanide anion causing displacement of the cyano group by the $S_N2$ mechanism with concomitant inversion of the chirality. Because the product isomer is less soluble than the epimer it will begin to crystallise out from the reaction mixture as soon as the solution becomes saturated with respect to the isomer, and this drives the process in favour of production of the less soluble isomer.

The polar organic solvents or diluents which may be used for the invention process are those in which the product isomer or racemic modification is less soluble than the epimer or racemate thereof. These may be for example monohydric lower alkanols containing up to six carbon atoms, such as isopropanol, isobutanol and t-butanol, or mixtures thereof. Other solvents or diluents include simple esters, such as ethyl acetate or mixtures with alkanes to obtain a medium which permits the isomer and the epimer to be separated on the basis of solubility difference. A proportion of water may be present, within the limits of miscibility, but this is usually less than 20% by volume.

Preferably the solvent is a branched lower alkanol such as isopropanol containing from 2 to 15% by volume of water.

The source of cyanide ions may be an alkali or alkaline earth cyanide, or a quaternary ammonium cyanide. Sodium cyanide and potassium cyanide are particularly preferred. It may be used in solid form, in which case any residual material at the conclusion of the process must be separated from the solid product by selective solubility, either by washing with water to dissolve the cyanide, or by extraction with an organic solvent to dissolve the product. Alternatively the cyanide may be in the form of an aqueous solution, which is used in excess may give rise to a two-phase system when certain solvents are used, in which case the process may be facilitated by the use of phase-transfer catalysts, such as the aforementioned quaternary ammonium cyanide. Preferably the cyanide is present in an amount of from 0.5 to 15 mole % of the epimer.

One convenient technique for isolating the product is to discharge the contents of the reaction vessel into an excess of dilute aqueous acid, such as sulphuric acid, or preferably a dilute aqueous solution of an alkali metal hypochlorite. This technique can be used with reaction mixtures involving cyanide in either solid or solution form, and permits recovery of the product by either filtration or solvent extraction.

The process is conducted in vessels in which the temperature may be controlled by external heating or cooling. The rate of deposition of the crystalline product is enhanced by reducing the solubility of the product by operating at lower temperatures, and by agitation of the vessel contents so as to provide thorough mixing. The period over which the process is conducted will depend upon the rate at which the product is formed, but is unlikely to be less than one hour or more than 60 hours. The precise conditions required will vary according to the particular product, but in general the process may be operated at a temperature in the range $-10°$ C. to $20°$ C. for a period of from 15 to 45 hours.

Although for some products the process can be conducted merely by adding the cyanide to a solution of the epimer and agitating the mixture at the relevant temperature for a period, it is often helful, especially for products having lower melting points or relatively higher solubility, to add a quantity of the product in solid crystalline form to the mixture so as to provide a crystalline surface on which further product can crystallise. The amount of added crystalline product is not critical provided that it is sufficient to provide a saturated solution with some remaining in the undissolved state at the particular operating temperature.

In order that the invention may be more clearly understood the following examples illustrate the use of the process for the production of lambda-cyhalothrin. As stated herein above lambda-cyhalothrin is a racemic product consisting of the isomer S-α-cyano-3-phenoxybenzyl 1R,3R-3-(Z-2-chloro-3,3,3-trifluoroprop-1-en-1-yl)-2,2-cyclopropane carboxylate and its enantiomer. Lambda-cyhalothin is obtained from cyhalothrin, which is produced as a mixture of four isomers in approximately equal amounts, the two isomers constituting lambda-cyhalothrin and the epimers of these two isomers, that is R-α-cyano-3-phenoxybenzyl 1R,3R-3-(Z-2-chloro-3,3,3-trifluoroprop-1-en-1-yl)-2,2-cyclopropane carboxylate and its enantiomer, respectively. For ease of reference these two pairs of isomers are referred to hereinafter as "Isomer Pair I" (lambda-cyhalothrin) and "Isomer Pair II".

EXAMPLE 1

Cyhalothrin (105 g), wet isopropanol containing 2.7 or 8.0% w/w water (270 g), sodium cyanide (6.5 g), and crystalline lambda-cyhalothrin are charged to a 1-liter glass vessel fitted with an twin turbine glass agitator and a cooling jacket and maintained at a temperature of $-5°$ C. by circulation of a cooled mixture of water and ethylene glycol with agitation for a period of 24 hours after which the ratio of Isomer Pair I/Isomer Pair II was determined by a gas chromatographic technique. The agitation is continued for a further 24 hours an a second determination of the I/II ratio mode.

The results are set out in Table I below in comparison with the results obtained for similar experiments in which diisopropylamine is present instead of cyanide.

TABLE I

| Agent | Isomer Pair I:II Ratio | | |
|---|---|---|---|
| | % Water | 24 hr | 48 hr |
| Sodium cyanide | 2.7 | 96.0 | 96.1 |
| Diisopropylamine | 2.7 | 93.6 | 95.1 |
| Sodium cyanide | 8.0 | 96.3 | 96.4 |
| Diisopropylamine | 8.0 | 94.9 | 96.5 |

From this it can be seen that the use of cyanide enables the process to proceed to substantial completion in about 24 hours, whereas the use of the amine requires a considerably longer period to achieve a similar end point.

We claim:

1. A process for obtaining lambda-cyhalothrin in the form of a racemic modification consisting of two isomers, namely S-α-cyano-3-phenoxybenzyl 1R,3R-3-(Z-2-chloro-3,3,3-trifluoroprop-1-en-1-yl)-2,2-dimethylcyclopropane carboxylate and its enantiomer which comprises the step of treating cyhalothrin in the form of a mixture of four isomers in approximately equal amounts, said four isomers being the two isomers constituting lambda-cyhalothrin and the epimers of these two isomers in solution in, or as a slurry in, a monohydric lower alkanol having up to six carbon atoms and optionally containing from 2 to 15% by volume of water with an alkali metal cyanide and in the absence of a base.

2. A process according to claim 1 in which the monohydric lower alkanol is isopropanol, isobutanol or t-butanol.

3. A process according to claim 1 in which the alkali metal cyanide is sodium cyanide or potassium cyanide.

4. A process according to claim 1 in which the cyhalothrin is treated as a solution in wet isopropanol.

5. A process according to claim 1 in which the cyhalothrin is treated as a slurry in wet isopropanol.

6. A process according to claim 1 in which the alkali metal cyanide is used in solid form.

7. A process according to claim 1 in which the alkali metal cyanide is used in the form of an aqueous solution in the presence of a phase transfer catalyst.

8. A process according to claim 1 conducted at a temperature of from $-10°$ to $20°$ C.

9. A process for obtaining lambda-cyhalothrin in the form of a racemic modification consisting of two isomers, namely S-α-cyano-3-phenoxybenzyl 1R,3R-3-(Z-2-chloro-3,3,3-trifluoroprop-1-en-1-yl)-2,2-dimethylcyclopropane carboxylate and its enantiomer which comprises the step of treating cyhalothrin in the form of a mixture of four isomers in approximately equal amounts, said four isomers being the two isomers constituting lambda-cyhalothrin and the epimers of these two isomers in solution in, or as a slurry in, wet isopropanol containing from 2 to 15% by volume of water with sodium cyanide in an amount of from 0.5 to 15 mole % based on cyhalothrin and in the absence of a base.

* * * * *